(12) United States Patent
Renzin et al.

(10) Patent No.: US 8,747,377 B2
(45) Date of Patent: *Jun. 10, 2014

(54) METHOD FOR TREATING SKIN IRRITATIONS SUCH AS DIAPER RASH AND THE LIKE

(75) Inventors: Stephen M. Renzin, Larchmont, NY (US); William Schmitt, Branford, CT (US)

(73) Assignee: Femaceuticals, LLC, Larchmont, NY (US)

( * ) Notice: Subject to any disclaimer, the term of this patent is extended or adjusted under 35 U.S.C. 154(b) by 1739 days.

This patent is subject to a terminal disclaimer.

(21) Appl. No.: 11/996,845

(22) PCT Filed: Aug. 3, 2006

(86) PCT No.: PCT/US2006/030144
§ 371 (c)(1),
(2), (4) Date: Feb. 11, 2008

(87) PCT Pub. No.: WO2007/019186
PCT Pub. Date: Feb. 15, 2007

(65) Prior Publication Data
US 2008/0195065 A1    Aug. 14, 2008

Related U.S. Application Data

(60) Provisional application No. 60/705,543, filed on Aug. 4, 2005.

(51) Int. Cl.
*A61F 13/15* (2006.01)

(52) U.S. Cl.
USPC ...................... 604/385.07; 604/290

(58) Field of Classification Search
USPC ............................. 604/290, 385.07
See application file for complete search history.

(56) References Cited

U.S. PATENT DOCUMENTS

| 3,340,153 A | 9/1967 | Kast |
| 3,483,008 A | 12/1969 | Herr |

(Continued)

FOREIGN PATENT DOCUMENTS

| DE | 665384 | 9/1938 |
| DE | 710483 | 9/1941 |

(Continued)

OTHER PUBLICATIONS

"Nutritional Components in Milk", Cornell University, Feb. 16, 2007.*

(Continued)

*Primary Examiner* — Lynne Anderson

(57) ABSTRACT

Various forms of skin irritations are treated with an appropriately configured and sized pad provided with a chilled skim milk additive which is useful for treating skin irritations such as diaper rash, irritations caused by incontinence, breast irritations experienced by nursing mothers, hemorrhoidal irritation, and skin irritations resulting from burns, insect bites, and the like. The irritated skin can be treated by applying the pad directly to the irritated skin. The treatment can continue during normal daily activities in various ways. The pad can take the form of breast pads that can be worn inside of a nursing bra, or it can take the form of an adhesive strip that can be adhered to the skin at the affected site. For treating diaper rash or incontinence-caused irritations, the pad can be placed in diapers or in suitable incontinence undergarments.

20 Claims, 3 Drawing Sheets

(56) References Cited

U.S. PATENT DOCUMENTS

| | | | |
|---|---|---|---|
| 3,959,491 A | 5/1976 | Young et al. | |
| 4,129,645 A | 12/1978 | Barnett et al. | |
| 4,240,436 A | 12/1980 | Singleton | 128/403 |
| 4,395,424 A * | 7/1983 | Veney | 514/722 |
| 4,460,571 A * | 7/1984 | Gomez | 424/70.14 |
| 4,540,567 A | 9/1985 | Oneto et al. | 424/45 |
| 4,556,146 A | 12/1985 | Swanson et al. | |
| 4,743,245 A | 5/1988 | Lassen et al. | 604/385 |
| 4,780,117 A | 10/1988 | Lahey et al. | 62/4 |
| 4,842,884 A | 6/1989 | Bookwalter et al. | |
| 4,986,076 A | 1/1991 | Kirk et al. | 62/4 |
| 5,167,655 A | 12/1992 | McCoy | |
| 5,428,016 A | 6/1995 | Tomita et al. | 514/15 |
| 5,645,830 A | 7/1997 | Reid et al. | 424/93.45 |
| 5,707,645 A | 1/1998 | Wierson | 424/436 |
| 6,004,551 A | 12/1999 | Reid et al. | 424/93.45 |
| 6,233,945 B1 | 5/2001 | Kohout | 62/4 |
| 6,241,715 B1 * | 6/2001 | Houser et al. | 604/385.07 |
| 6,393,843 B2 | 5/2002 | Kohout | 62/4 |
| 6,468,526 B2 | 10/2002 | Chrisope | |
| 6,695,678 B1 * | 2/2004 | Foley et al. | 450/57 |
| 6,761,885 B1 | 7/2004 | Hakansson et al. | 424/93.45 |
| 6,916,334 B2 * | 7/2005 | Noonan | 607/108 |
| 6,972,010 B2 | 12/2005 | Pesce et al. | |
| 7,008,409 B2 * | 3/2006 | Spiezio et al. | 604/385.07 |
| 2003/0036740 A1 | 2/2003 | Hammonds et al. | 604/385.04 |
| 2003/0105445 A1 * | 6/2003 | Lange et al. | 604/385.07 |

FOREIGN PATENT DOCUMENTS

| | | | |
|---|---|---|---|
| FR | 2 864 445 | 7/2005 | 7/48 |
| JP | 61-172126 | 10/1986 | |
| JP | 9-291024 | 11/1997 | |
| JP | 2001-299801 | 10/2001 | |
| RU | 2183935 | 6/2002 | |
| WO | WO 9917813 | 4/1999 | |
| WO | WO 2004032985 | 5/2004 | |

OTHER PUBLICATIONS

The Natural Baby Catalog, http://naturalbaby.stores.yahoo.net/babybee.html, 2005.
BabiesExpress, http://babiesexpress.com/by2055/html, 2000.
Brent et al., "Sore nipples in breast-feeding women: a clinical trial of wound dressings vs conventional care," Archives of Pediatrics & Adolescent Medicine, Nov. 1998, vol. 152, No. 11, pp. 1077-1082.
Morland-Schultz et al., "Prevention of and therapies for nipple pain: a systematic review," Journal of Obstetric, Gynecologic, and Neonatal Nursing: NOGNN/NAACOG, Jul.-Aug. 2005, vol. 34, No. 4, pp. 428-437.
European Search Report.

* cited by examiner

METHOD FOR TREATING SKIN IRRITATIONS SUCH AS DIAPER RASH AND THE LIKE

Applicant hereby claims priority benefits of PCT Patent Application No. PCT/US06/30144 filed Aug. 3, 2006, which claims the benefit of U.S. Provisional Patent Application No. 60/705,543 filed Aug. 4, 2005, the disclosures of which are herein incorporated by reference.

TECHNICAL FIELD

This invention relates to a device for treating skin irritations such as diaper rash, irritations caused by incontinence, breast irritations experienced by nursing mothers, hemorrhoidal irritation, and skin irritations resulting from burns, exercise friction, tight fitting clothing, insect bites, and the like. The device includes a source of cold and a pad which contains dry milk, which pad is applied directly to the irritated skin area and can be worn over the irritated skin area during normal everyday activities.

BACKGROUND ART

Various forms of skin irritations are common place. These include diaper rash experienced by infants, irritations caused by incontinence experienced by senior citizens among others, breast nipple inflammation experienced by nursing mothers, hemorrhoidal irritation, and skin irritations resulting from burns, exercise friction, tight fitting clothing, insect bites, and the like.

These problems have been addressed in a number of different ways, depending on the source and nature of the skin irritation. Hemorrhoidal inflammation and irritation has been dealt with by applying substances such as petrolatum, cocoa butter and/or starch to the affected area. Breast nipple irritation and inflammation has been dealt with by applying breast pads containing calamine, petrolatum and/or dimethicone to the affected areas. The pads can be worn inside of nursing bras. Diaper rash irritation and inflammation has been dealt with by applying dimethicone, petrolatum and/or zinc oxide to the affected areas. Burns, insect bites and other skin irritations may be treated with cocoa butter, antibiotics and/or disinfectants and adhesive strip bandages which cover the affected areas.

It would be desirable to provide a readily usable single solution to all of the aforesaid skin inflammation and irritation problems that would reduce the acidity of the tissues in question, while soothing the irritation encountered. The product incorporating the solution to the problem should be readily usable during daily activity of the subject, be non-messy, and be relatively inexpensive and simple to produce, without requiring FDA approval.

DISCLOSURE OF THE INVENTION

This invention is directed to the use of a pad which incorporates a milk ingredient that, when applied to the irritated tissue will lower the acidity of the tissue and, because of other materials such as proteins in the milk, soothe the inflamed area. The pad can contain a refrigerant that can be made cold by crushing, or it can contain a gel that can be cooled by being placed in a refrigerator or freezer. The pad can be configured in appropriate forms which are shaped so as to obtain intimate contact with the individual's skin at the area wherein the irritation to be treated is located. The milk component can be incorporated into the pad in a number of different ways. For example it has been found that slurries of nonfat dry milk in water can be formed, sprayed onto the pad, dried and then are suitable for use; alternatively, slurries of nonfat dry milk and a meltable anhydrous water-soluble carrier such as polyethylene glycol can be formed. Alternatively, a slurry of nonfat dry milk and a non-water-soluble carrier such as mineral oil and wax can be formed. A slurry of nonfat dry milk and an aqueous solution of thickeners and polymers can be formed. The aforesaid dry milk can be substituted with non-dry milk, and whole milk, and both liquid and dry can be used in place of the nonfat milk component. Nonfat dry milk is preferred. When a liquid milk product, either whole or nonfat, is used, the milk product would be dried after being applied to the pad. Any combination of the dry or liquid milk components, either nonfat, or whole milk, can be used in producing the pad.

When using a wet slurry production protocol, the pad should be provided with a non-woven outer cover onto which the milk component is coated. The outer cover can be made from polyethylene, polypropylene, poly amides, such as nylon, PET, rayon, cellulose, cotton, viscose, acrylics and fibers from wood pulp. The non-woven covers can be made by spin bonding, melt blowing, needle punching, resin bonding, air laying, hydro entangling, caustic entangling, wet laying, spin lacing and carding, depending on which of the materials are being used to make the cover. The milk component can be applied to the pad cover before assembly of the pad, i.e., before the pad is placed in the pad cover, or after assembly of the pad. The milk coating can be applied to the pad cover by a doctor blade, by rollers, or by spraying. When an aqueous solution of the milk component is used, the coated pad or pad cover must be dried before the pad is ready for use. Drying can be accomplished either by forced air drying or by direct application of heat through forced hot air, heated rollers, bars or plates. The pad assembly can include the absorbent filler pad, polymers, such as high molecular weight acrylics, commonly referred to as "super slurpers", to hold moisture and may also include a pouch containing a liquid which can be refrigerated and slipped into the pad.

The finished pad assembly is used in the following manner. When the milk is applied to an outer non-woven pad cover, the dried milk constituent will be in intimate contact with the subject's skin. It should be realized that when the milk slurry is dried on the pad's outer surface, the concentration of milk on the pad will be more highly concentrated than if milk were to be used without drying the milk coating. Thus, the natural moisture of the skin will dissolve or release the fat-free or whole milk to the skin. This result can be accelerated by having a semi-permeable sheet material between the outer non-woven cover and the interior of the pad. The cover serves to prevent transepidermal moisture from bypassing the dried milk, and ensures that the transepidermal moisture will solubilize the dried milk solids into a milk solution or mixture. The use of such a sheet material will increase the concentration of transepidermal water vapor such that the water vapor will enhance release of milk to the affected area.

In the case of application of the milk constituent to the assembled pad, the concentration of milk on the exterior and interior of the pad will depend on how it is applied, i.e., by coating cylinder or by spray. Use of a cylinder which directly contacts the non woven sheet material to coat the sheet material will result in a greater concentration of milk on the sheet material due to the direct contact that occurs between the cylinder and the sheet material. The concentration of milk in the pad will be able to be thus controlled along with the formulation type, i.e., either hydrophobic or hydrophilic, to affect both instant and/or sustained release of milk from the pad to the affected area. A hydrophilic formulation will more readily result in release of the milk for the pad assembly because of the transepidermal moisture. If the formulation is hydrophilic, milk release can be slowed by increasing the molecular weight of the incorporated material. Polyethylene glycol is one example of such a material. If the material is hydrophobic, materials such as silicone can be used to retard the release of the milk constituent. Thus, the pad assembly can be customized to a certain degree regarding the rate of release of the milk constituent. A preferred embodiment of the pad assembly could employ an accelerated release of the milk constituent initially, followed by a slower, more sustained release of the milk constituent. The use of a polyethylene glycol matrix which includes different molecular weight fractions would achieve this desired result.

The pad assembly can be impregnated with the milk component in a number of other ways which do not involve the formation of a milk slurry per se. One way would be to spray or coat the pad material with water, or an aqueous slurry of a sticky substance, and then sprinkle dry milk on the wet pad material. The sprinkled pad material would then be dried. One could also spray or coat the pad material with a concentrated solution or slurry or a non-concentrated solution of wet milk and then dry the milk-coated material. Another way to produce the milky material would be to add milk to a solid polymer which is to be used to form the non-woven component of the pad assembly after the polymer is melted before it is converted into a fiber form, and then run the polymer-milk mixture through a spinneret so that the milk is incorporated into the polymer fiber.

BRIEF DESCRIPTION OF THE DRAWINGS

This invention will be more readily understood from the following detailed description of a preferred embodiment thereof when taken in conjunction with the accompanying drawings wherein.

DETAILED DESCRIPTION OF THE INVENTION

Figure 1:
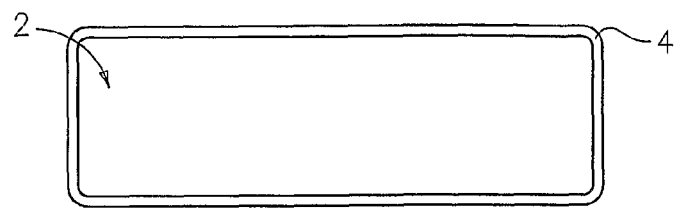
FIG. 1 is a plan view of a first embodiment of a pad assembly which is formed in accordance with this invention.
Figure 2:
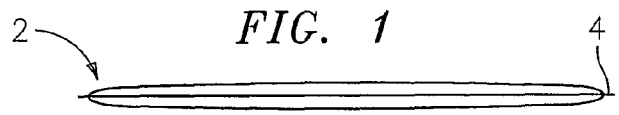
FIG. 2 is a side elevational view of the pad assembly of FIG. 1.
Figure 3:
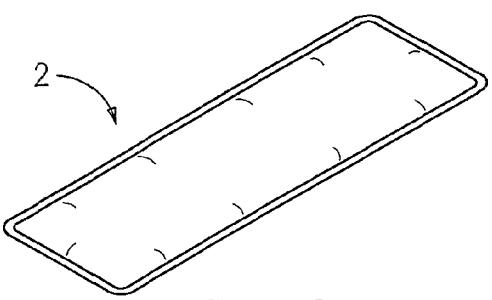
FIG. 3 is perspective view of the pad assembly of FIG. 1.
Figure 4:
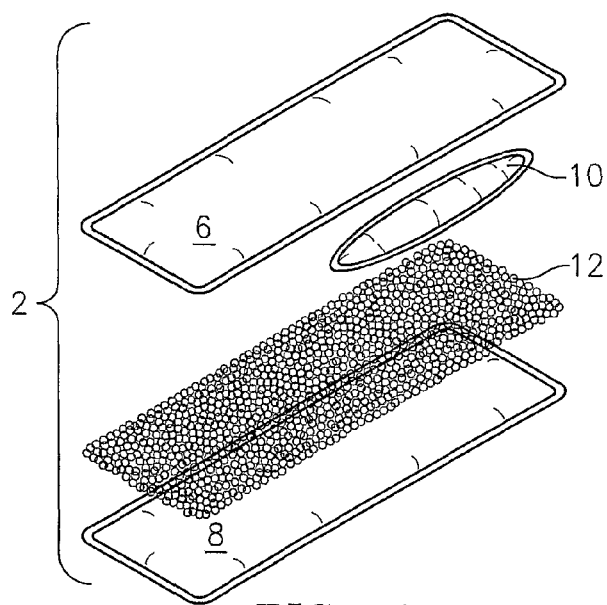
FIG. 4 is an exploded view of the pad assembly of FIG. 1.
Figure 4A:
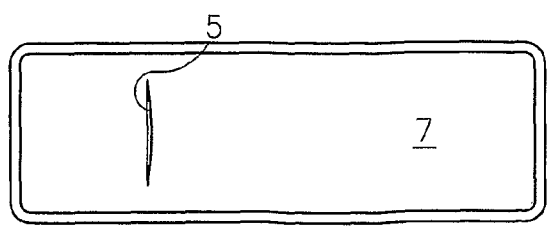
FIG. 4a is a plan view of an outer pouch component which may be used to house the assembly of FIG. 1.
Figure 5:
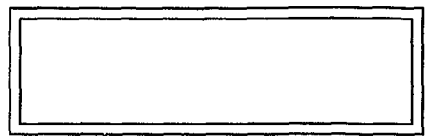
FIG. 5 is a plan view of a core component of a second embodiment of a pad assembly which is formed in accordance with this invention.
Figure 6:
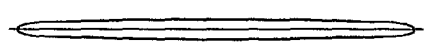
FIG. 6 is a side elevational view of the core component of FIG. 5.
Figure 7:
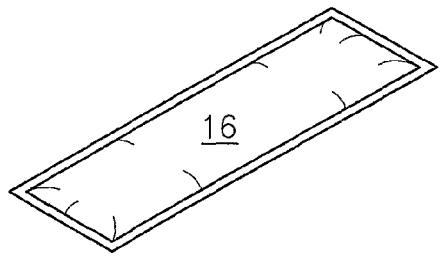
FIG. 7 is perspective view of the core component of FIG. 5.
Figure 8:
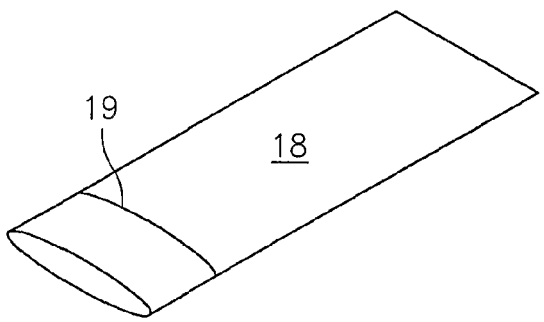
FIG. 8 is a perspective view of a sleeve component of the second embodiment of a pad assembly.

Referring now to the drawings, there is shown in FIGS. 1-4a, a first embodiment of a pad assembly which is formed in accordance with this invention, and which is designated generally by the numeral 2. This pad assembly 2 is a disposable assembly which requires refrigeration prior to use. The pad assembly 2 has outer components 6 and 8 which are formed from a non-woven sheet material that is impregnated with nonfat dry milk. The sheets 6 and 8 deliver the milk constituent of the pad assembly 2 to the tissues when the pad assembly 2 is worn. An inner component 10 of the pad assembly 2 contains a material that can be refrigerated, to provide the cold required by the pad assembly 2. A further optional inner component 12 is a layer of exothermic beads which may be ammonium nitrate for example. The several components of the pad 2 may be formed as a pouch by sealing or otherwise adhering the edges 4 of the two sheets 6 and 8 together. The assembly 2 can be made reusable by inserting it through a slit 5 into an outer permeable pouch 7 shown in FIG. 4a which will directly contact the affected tissues and will allow through passage of the milk to the affected tissues. Alternatively, the outer pouch 7 may be impregnated with dry nonfat milk. The pouch 7 will be provided with adhesive strips (not shown) to facilitate securement of the assembly to the user's skin or to garments, such as diapers or incontinence undergarments. If the pouch 7 is used, after the assembly is used, the inner assembly 2 can be removed from the pouch 7, and the pouch 7 can be discarded. The inner assembly 2 can then be refrigerated again and placed in another pouch for further use.

Figure 9:
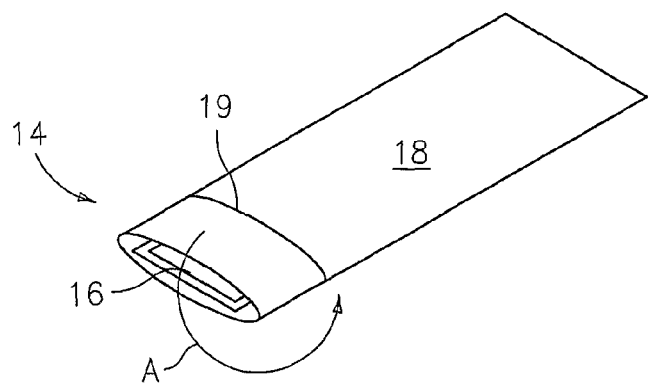
FIG. 9 is a perspective view of the assembled pad assembly indicating how the core component is inserted into the sleeve component.

FIGS. 5-9 disclose a second embodiment of the pad assembly which is a single use embodiment that does not require refrigeration. This second embodiment includes a core component 14 in the form of a pouch which contains a crushable endothermic refrigerant compound which, when squeezed, or crushed, provides the necessary cold for the assembly to operate properly. The crushable refrigerant can include endothermic reaction compounds of the types described in U.S. Pat. No. 4,780,117 Lahey; U.S. Pat. No. 4,986,076 Kirk; U.S. Pat. No. 6,233,945 Kohout; and U.S. Pat. No. 6,393,843 Kohout, the contents of which are incorporated into this application in their entirety. An outer sleeve 18 which is formed from a non woven material is also included. The outer sleeve 18 is coated or impregnated with non fat dry milk. The sleeve 18 has three sealed edges and one open end. The sleeve 18 may also be formed with a fold line 19 which allows the sleeve 18 to be closed after the core 16 is placed in the sleeve 18, as shown in FIG. 9. The open end of the sleeve 18 is simply folded back as indicated by the arrow A and a strip of tape will be used to secure it in place. In the single use version of the pad assembly the entire assembly is discarded after use thereof. The sleeve 18 can be provided with adhesive strips (not shown) to facilitate securement of the assembly to the user's skin or garments, such as diapers or incontinence undergarments.

Figure 10:
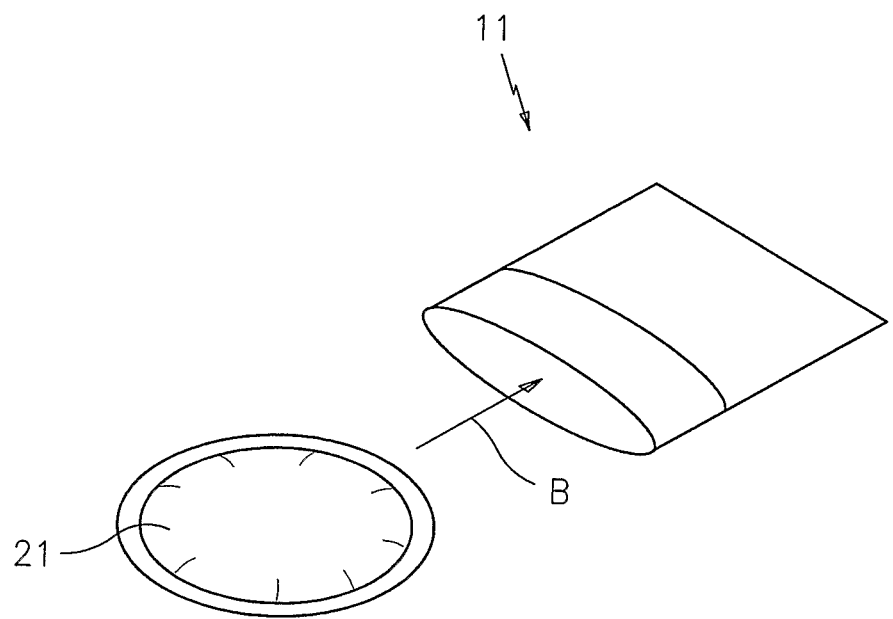
FIG. 10 is a plan view of a pad which takes the form of a breast pad that can be worn in a nursing bra when being applied to the breasts of the nursing mother or nipple irritation from ill fitting or tight clothing, or exercise.

FIG. 10 shows an embodiment of the pad which is configured for use by nursing mothers to counteract nipple inflammation which results from breast feeding of newborns or other causes of breast irritation. The pad includes an outer sleeve denoted generally by the numeral 11 which contains the milk component of the assembly. The coolant component is denoted by the numeral 21 and preferably takes the form of a circular pouch which contains the coolant material. The pouch 21 is inserted into the sleeve 11 as indicated by the arrow B and the sleeve 11 is closed in the same manner as shown in the embodiment disclosed in FIG. 9. The assembled pads are then positioned over the subject's nipples and can be held in place, for example, by a bra, such as a nursing bra. The pad can be reversed once the milk component on one side thereof is depleted.

Figure 11:
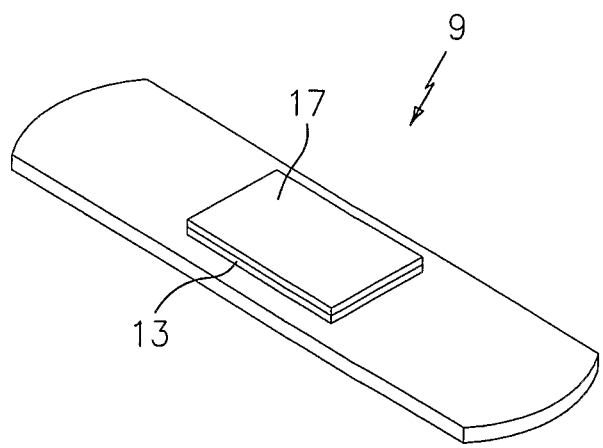
FIG. 11 is a plan view of a pad which takes the form of a self adhesive bandage such as an adhesive strip for use in connection with insect bites, burns and the like localized skin irritations.

FIG. 11 shows an embodiment of the pad which is disposed on an adhesive strip 9 which can be used to treat irritation from insect bites, burns or other similar skin irritations. The adhesive strip 9 includes a milk-containing component 17 which will directly contact the affected skin area. The coolant-containing component 13 is disposed beneath the component 17. The adhesive strip is positioned over the burn or insect bite with the component 17 of the strip directly overlying and contacting the burn or insect bite or other skin irritation.

With all embodiments of the pad assembly, when the assembly is worn, the milk impregnated component will be disposed against the affected tissue. This allows transepidermal moisture to penetrate the milk impregnated component so as to moisten the dried milk in the component. It will be readily appreciated that the pad assembly of this invention provides a simple, reliable and convenient treatment whereby skin irritation can be relieved. The pad assembly can be worn during most common daily activities and is not restricted to in-house usage. The pad assembly is not messy to use, and extended use of it will not result in any adverse effects to the user.

When treating diaper rash or skin irritations occurring in connection with the use of incontinence undergarments, the pad described herein above can be incorporated into or placed in a diaper or an incontinence undergarment. When treating breast irritations resulting from nursing, the subject pad can be configured in the form of an insert for a bra for the nursing mother. When treating skin irritations resulting from burns or from insect bites, the pad can be placed in bandages, or miniaturized and placed in, or incorporated into adhesive strips. In each of these aforesaid additional uses, the pad will comprise a cold pack covered by a fabric in which milk is incorporated in any of the forms described herein above.

Since many changes and variations of the disclosed embodiments of the invention may be made without departing from the inventive concept, it is not intended to limit the invention otherwise than as required by the appended claims.

What is claimed is:

1. A method for treating inflammation of a woman's breast nipples, said method comprising:
   a) covering the nipples with an absorbent pad which contains a cooling component and a dry milk component, said milk component contacting the nipples; and
   b) retaining said pad in contact with the nipples during the period of treatment.

2. The method of claim 1 wherein said pad is disposed in a bra.

3. The method of claim 1 wherein said pad further comprises a cover component in which said absorbent pad component is disposed.

4. The method of claim 1 wherein said cooling component is a freezable substance.

5. The method of claim 1 wherein said cooling component is a gel.

6. The method of claim 1 wherein said cooling component is an endothermic substance.

7. The method of claim 1 wherein said milk component is nonfat milk.

8. The method of claim 1 wherein said milk component is formed from a slurry of dry milk and a meltable anhydrous water-soluble carrier.

9. The method of claim 8 wherein said meltable anhydrous water-soluble carrier is polyethylene glycol.

10. The method of claim 1 wherein said milk component is formed from a slurry of dry milk and a non-water soluble carrier.

11. The method of claim 10 wherein said non-water soluble carrier is mineral oil and wax.

12. The method of claim 1 wherein said absorbent pad is disposed in
   a cover component, said cover component being formed from a non-woven fibrous material, and said milk component being in the form of a dried coating on said cover.

13. The method of claim 12 wherein the cover component is formed from a solid polymer into which the milk component is incorporated prior to conversion of the polymer to a fibrous form.

14. The method of claim 1 wherein said milk component is a solution or slurry formed from dry milk and water.

15. A method for treating skin irritations and/or inflammation resulting from breast feeding of newborns, diaper rash, incontinence
   rash, hemorrhoids, burns, insect bites, and the like, said method comprising:
   a) covering the skin irritation with an absorbent pad which contains a cooling component and a dry milk component, said milk component contacting the skin irritation/inflammation; and
   b) retaining said pad in contact with the skin irritation/inflammation during the period of treatment.

16. The method of claim 15 wherein the skin irritation/inflammation is the result of a burn or insect bite, and the pad is a component of an adhesive strip which covers the burn or insect bite.

17. The method of claim 15 wherein the skin irritation/inflammation is nipple irritation that is the result of breast feeding of a newborn infant, and the pad is a component of a nursing bra which covers the nipples.

18. The method of claim 15 wherein the skin irritation/inflammation is the result of diaper rash, and the pad is a component of a diaper which covers the diaper rash.

19. The method of claim 15 wherein the skin irritation/inflammation is the result of a hemorrhoid, and the pad is a component of an adhesive strip which covers the hemorrhoid.

20. The method of claim 15 wherein the skin irritation/inflammation is the result of incontinence, and the pad is a component of an undergarment designed to deal with incontinence.

* * * * *